United States Patent [19]

Weeks et al.

[11] 4,390,709
[45] Jun. 28, 1983

[54] PREPARATION OF GAMMA-PYRONES

[75] Inventors: Paul D. Weeks, Gales Ferry; Robert P. Allingham, Groton, both of Conn.

[73] Assignee: Pfizer Inc., New York, N.Y.

[21] Appl. No.: 371,932

[22] Filed: Apr. 26, 1982

Related U.S. Application Data

[60] Division of Ser. No. 741,112, Nov. 11, 1976, Pat. No. 4,342,697, which is a continuation-in-part of Ser. No. 608,452, Aug. 28, 1975, abandoned.

[51] Int. Cl.³ .......................................... C07D 309/38
[52] U.S. Cl. .................................................... 549/418
[58] Field of Search ........................................ 549/418

[56] References Cited

U.S. PATENT DOCUMENTS

| | | | |
|---|---|---|---|
| 3,063,985 | 11/1962 | Zderic | 260/345.9 R |
| 3,455,960 | 7/1969 | Schleppnik et al. | 260/345.9 R |
| 3,476,778 | 11/1969 | Schleppnik et al. | 260/345.8 R |
| 3,707,482 | 12/1972 | Laliberte | 260/345.8 R |
| 3,751,434 | 8/1973 | Lefebvre | 260/345.9 |
| 4,059,595 | 11/1977 | Shono et al. | 260/345.9 R |

OTHER PUBLICATIONS

Clauson-Kaas et al., ACTA Chem Scand., 6, 531 (1952).
Clauson-Kaas et al., ibid 7, 845 (1953).
Laliberté et al., J. Med. Chem. 16, pp. 1084–1089 (1973).
Achmatowicz et al., Tetrahedron 32, pp. 1051–1054, (1976).
Achmatowicz Jr. et al., Tetrahedron, vol. 27, 1971, pp. 1973–1996.
Paulsen et al., Tetrahedron Letters, No. 49–50, pp. 4377–4380, (1974).

*Primary Examiner*—Nicky Chan
*Attorney, Agent, or Firm*—Connolly and Hutz

[57] ABSTRACT

Maltol (3-hydroxy-2-methyl-gamma-pyrone) is prepared from furfural through intermediates (a) 1-(2-furyl)-1-ethanol; (b) 2-(1-hydroxyethyl)-2,5-dialkoxy-2,5-dihydrofuran; (c) alkyl or aralkyl-2-methyl-2H-pyran-3(6H)-one; and (d) 2-alkyl or aralkyl-4-methyl-3,7-dioxabicyclo[4.1.0]heptan-5-one.

Pyromeconic acid (3-hydroxy-gamma-pyrone), ethyl maltol (3-hydroxy-2-ethyl-gamma-pyrone) and other valuable 2-substituted-3-hydroxy-gamma-pyrones are prepared in an analogous manner from furfural.

4 Claims, No Drawings

PREPARATION OF GAMMA-PYRONES

CROSS-REFERENCE TO RELATED APPLICATIONS

This application is a division of copending application Ser. No. 741,112, filed Nov. 11, 1976, now U.S. Pat. No. 4,342,697, which in turn is a continuation-in-part of application Ser. No. 608,452, filed Aug. 28, 1975, now abandoned.

BACKGROUND OF THE INVENTION

Maltol is a naturally occurring substance found in the bark of young larch trees, pine needles and chicory. Early commercial production was from the destruction distillation of wood. Synthesis of maltol from 3-hydroxy-2-(1-piperidylmethyl)-1,4-pyrone was reported by Spielman and Freifelder in J. Am. Chem. Soc., 69, 2908 (1947). Schenck and Spielman, J. Am. Chem. Soc., 67, 2276 (1945), obtained maltol by alkaline hydrolysis of streptomycin salts. Chawla and McGonigal, J. Org. Chem., 39, 3281 (1974) and Lichtenthaler and Heidel, Angew. Chem., 81, 998 (1969), reported the synthesis of maltol from protected carbohydrate derivatives.

Synthesis of gamma-pyrones such as pyromeconic acid, maltol, ethyl maltol and other 2-substituted-3-hydroxy-gamma-pyrones are described in U.S. Pat. Nos. 3,130,204; 3,133,089; 3,140,239; 3,159,652; 3,365,469; 3,376,317; 3,468,915; 3,440,183; and 3,446,629.

Maltol and ethyl maltol enhance the flavor and aroma of a variety of food products. In addition, these materials are used as ingredients in perfumes and essences. The 2-alkenylpyromeconic acids reported in U.S. Pat. No. 3,644,635 and the 2-arylmethylpyromeconic acids described in U.S. Pat. No. 3,365,469 inhibit the growth of bacteri and fungi and are useful as flavor and aroma enhancers in foods and beverages and aroma enhancers in perfumes.

SUMMARY OF THE INVENTION

This invention is concerned with a process for preparing gamma-pyrones of the formula:

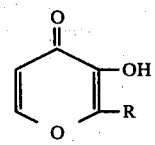

wherein R is hydrogen, lower alkyl of 1 to 6 carbon atoms, lower alkenyl of 2 to 6 carbon atoms, phenyl or benzyl.

Maltol (3-hydroxy-2-methyl-gamma-pyrone) is prepared from furfural through intermediates (a) 1-(2-furyl)-1-ethanol; (b) 2-(1-hydroxyethyl)-2,5-dialkoxy-2,5-dihydrofuran; (c) alkyl or aralkyl-2-methyl-2H-pyran-3(6H)-one; and (d) 2-alkyl or aralkyl-4-methyl-3,7-dioxabicyclo[4.1.0]heptan-5-one.

Other valuable 2-substituted-3-hydroxy-gamma-pyrones are prepared in an analogous manner from furfural.

DETAILED DESCRIPTION OF THE INVENTION

This invention is concerned with the preparation of 2-substituted-3-hydroxy-gamma-pyrones utilizing furfural as the starting material. Furfural is an inexpensive raw material which is prepared industrially from pentosans which are contained in cereal straws and brans.

As used throughout the specification and claims, the term "lower alkyl" and the lower alkyl portion of alkoxy embraces both straight and branched chain alkyl radicals containing from one to six carbon atoms; the term "lower alkenyl" embraces straight and branched chain alkenyl groups containing from two to six carbon atoms; the term "aryl" denotes a monocyclic aromatic hydrocarbon of six to eight carbon atoms; and the term "aralkyl" encompasses lower alkyl groups in which aryl as defined above is substituted for a hydrogen atom.

The reactions involved in the present invention are outlined as follows:

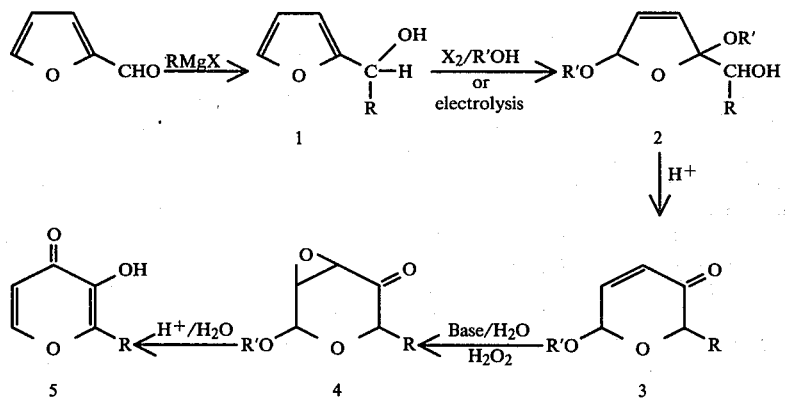

Intermediates:
R' = alkyl
R = hydrogen, alkyl, aryl, alkenyl, aralkyl
Final Product (5):
R = hydrogen, alkyl, alkenyl, aryl, aralkyl
R = H, pyromeconic acid
R = CH$_3$, maltol
R = CH$_2$CH$_3$, ethyl maltol Intermediate 2 (R = CH$_3$) is described in Acta Chem. Scand., 9, 17 (1955) and Tetrahedron 27, 1973 (1971).

Intermediate 2 (R=CH₂CH₃) is a new compound which can be made by methods already described.

The treatment of intermediate 2 with a strong acid is novel and it produces the desired alkoxy derivative 3 directly in high yield and avoids the formation of the corresponding hydroxy derivative which is very unstable to further reactions. Intermediate 2 is contacted with an essentially anhydrous acid. The presence of a protic solvent such as an alcohol or a small amount of water is actually beneficial. Following this treatment, the product, in a state of purity suitable for conversion to intermediate 3, is separated from the acid medium by conventional extraction techniques. Although formic and trifluoroacetic acids are preferred, any acid with a pKa of approximately 4 or below will convert intermediate 2 to the desired intermediate 3. Other suitable organic acids include p-toluenesulfonic acid, methanesulfonic acid, citric acid, oxalic acid and chloroacetic acid; suitable mineral acids include sulfuric acid, hydrochloric acid, hydrofluoric acid and phosphoric acid.

Acidic resins such as Amberlite GC-120 and Dowex 50W may also be employed.

The reaction, usually conducted at ambient temperature, may be carried out at a temperature range of −40° to 35° C. The preferred temperature range is 20° to 30° C.

Kaas et al in Acta Chem. Scand., 6, 545 (1952) and 7, 845 (1953) report the production of a ketal of structure 7 from the tetrahydrofuran 6 whereas the process of the present invention produces the desired ketone 9 from the dihydrofuran 8.

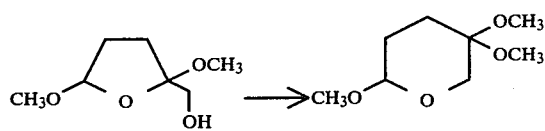

6        7

-continued

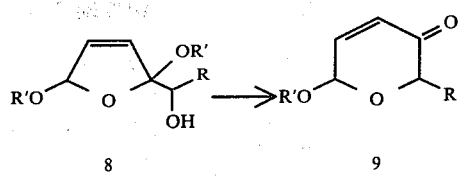

8        9

In fact, the treatment of compound 6 using alkanol and strong mineral acids such as HCl or H₂SO₄ at much lower temperature than those employed by Kaas et al leads to the formation of compounds 10 and 11. The formation of these compounds, rather than compound 12, clearly shows that the double bond is not inert under conditions similar to those employed by Kaas. The double bond in fact reacts with methanol at a rapid rate to form 10 or 11, compounds which are not useful in the present invention since they cannot be epoxidized under our process conditions.

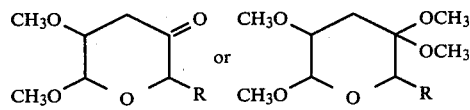

10        11

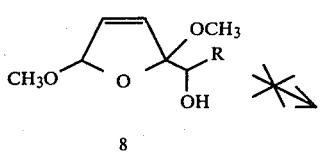

8

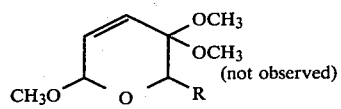

12

The epoxidation of intermediate 3 to the epoxy ketone 4 is a new and novel process. Intermediate 3 is dissolved in a suitable solvent such as water or an alcohol such as isopropyl alcohol or methanol. A base such as sodium bicarbonate or sodium hydroxide is added followed by the addition of H₂O₂ (30%). The reaction is conducted at a temperature range of −10° to 15° C. for about 1 to 2 hours. The desired intermediate 4 can be separated by conventional extraction techniques, and is suitable for rearrangement to the desired pyrone 5 without further purification.

The final rearrangement of the epoxy ketone 4 to the gamma-pyrone 5 is novel and proceeds in good yield and purity. Intermediate 4 is heated in an aqueous acid solution at a temperature range of 25° to 160° C. for about 1 to 3 hours. The preferred reaction condition is heating in aqueous solution containing a mineral acid such as hydrochloric acid or sulfuric acid at a temperature range of 80°–110° C. for about 1 to 3 hours. The conversion of intermediate 4 to product 5 can also be effected by the use of Lewis acids such as boron trifluoride etherate, zinc chloride and tin tetrachloride; by acidic resins such as Amberlite GC-120 or Dowex 50W; and by strong organic acids such as p-toluenesulfonic acid or formic acid. The isolation of the desired gamma-pyrone 5 is effected by conventional crystallization or extraction techniques. The gamma-pyrone may be recrystallized from an appropriate solvent such as isopropanol, methanol or water.

Compounds related to intermediate 3 (R=CH₂OH or R=CH₂O-alkyl) can be prepared from carbohydrate sources as described in Accounts of Chemical Research 8, 192 (1975). By the process of the present invention, these compounds can be converted to intermediate 4 and product 5 where R=CH₂OH or CH₂O-alkyl. Product 5 (R=CH₂OH or CH₂O-alkyl) can be converted to maltol as described in U.S. Pat. No. 3,130,204 or Angew. Chem. 81, 998 (1969).

EXAMPLE 1

In a 3 neck-roundbottom flask equipped with a magnetic stirring bar, a jacketed addition funnel, a thermometer and a dry ice condensor was added 22.4 g (0.2 mol) of intermediate 1 (R=CH₃), 100 ml of methanol and 21.1 g (0.2 mol) of sodium carbonate, and this mixture cooled to 0° C. using an ice-acetone bath. To this rapidly stirred solution was then added dropwise a cold (−30°) solution of chlorine (11.0 ml, 0.24 mol) in methanol. The addition of chlorine was controlled to keep the reaction temperature under 40° C. The addition required about 2 hours. After the addition, the reaction mixture was stirred at ice bath temperature for 30 minutes, and then allowed to warm to room temperature. The resulting slurry was filtered, the methanol removed in vacuo, the residue taken up in benzene and passed through an alumina plug as a final filter. Removal of the benzene provided 31.9 g. (91%) of of the desired dimethoxy dihydrofuran 2 (R=CH₃, R'=CH₃). This material can be used without further purification or it can be distilled, b.p. 76°–78°/5 mm [104°–107°/10–11 mm, Acta Chem. Scand. 9, 17 (1955)].

| | Analysis: | |
|---|---|---|
| | C | H |
| Calc'd. for C₈H₁₄O₄: | 55.22 | 8.11 |
| Found: | 55.34 | 8.04 |

EXAMPLE 2

The method of Example 1 was repeated with intermediate 1 (R=H) to yield intermediate 2 (R=H, R'=CH₃), b.p. 80°–82°/5 mm [71°/1.0 mm, Tetrahedron 27, 1973 (1971)].

EXAMPLE 3

The method of Example 1 was repeated with intermediate 1 (R=CH₂CH₃) to yield intermediate 2 (R=CH₂CH₃, R'=CH₃) b.p. 102°/10 mm.

| | Analysis: | |
|---|---|---|
| | C | H |
| Calc'd. for C₉H₁₆O₄: | 57.50 | 8.58 |
| Found: | 57.39 | 8.59 |

EXAMPLE 4

The method of Example 1 was repeated using intermediate 1 (R=CH₃) replacing methanol with isopropanol to yield intermediate 2 [R=CH₃, R'=CH(CH₃)₂], b.p. 62°–64°/0.05 mm.

EXAMPLE 5

The method of Example 1 may be repeated using bromine instead of chlorine using intermediate 1 to yield intermediate 2 where R is hydrogen, methyl, ethyl, hexyl, phenyl, benzyl, vinyl, 1-butenyl, allyl and 1-hexenyl; and R' is methyl, ethyl, isopropyl and hexyl.

EXAMPLE 6

In a small glass electrolysis vessel having a carbon anode and nickel cathode was placed 50 ml of methanol, 0.5 ml of concentrated sulfuric acid, and 1.12 g. (0.01 mol) of the intermediate 1 (R=CH₃, R'=CH₃) and the solution cooled to −20° C. An electrolysis was then carried out using a potentiostat/galvanostat Princeton Applied Research Corporation Model 373 instrument set to deliver a constant current of 0.6 amperes. After a reaction time of 30 minutes, the reaction was poured into water and the product 3 (R=CH₃, R'=CH₃), isolated by a chloroform extraction procedure. This procedure is similar to that described in U.S. Pat. No. 2,714,576 with sulfuric acid replacing ammonium bromide as the electrolyte.

EXAMPLE 7

The method of Example 6 may be repeated with intermediate 1 to yield intermediate 2 where R is hydrogen, ethyl, hexyl, phenyl, benzyl, vinyl, allyl, 1-butenyl or 1-hexenyl; and R' is ethyl, isopropyl or hexyl.

EXAMPLE 8

To a 2-liter, 3-neck roundbottom flask equipped with a magnetic stirrer, dropping funnel and a thermometer was added 400 ml of formic acid and 20 ml of methanol. To this solution at 25° C. was added a solution of intermediate 2 (R=CH₃, R'=CH₃) 104.4 g., 0.6 mol, in 40 ml of methanol. The dropwise addition required 15 minutes and was maintained at a temperature of 20° to 30° C. The reaction mixture was then poured into a liter of water and extracted 3 times with 500 ml portions of chloroform. The combined chloroform extracts were washed with an aqueous sodium bicarbonate solution and then with brine. The chloroform solution was evaporated to a crude yield of 76 g (89%) of intermediate 3 (R=CH₃, R'=CH₃) as a light brown product. The crude material may be used as such or distilled at 2 mm pressure, 50°–52° C. [82°–85° C./30 mm, Tetrahedron 27, 1973 (1971)].

EXAMPLE 9

The method of Example 8 was repeated with analogous intermediate 2 (R=H, R'=CH₃) to yield intermediate 3 (R=H, R'=CH₃), b.p. 60°–66° C./14 mm [76°–81° C./23 mm, Tetrahedron 27, 1973 (1971)].

EXAMPLE 10

The method of Example 8 was repeated with intermediate 2 (R=CH₂CH₃, R=CH₃) to yield intermediate 3 (R=CH₂CH₃, R'=CH₃), b.p. 79°–80° C./14 mm.

EXAMPLE 11

The method of Example 8 may be repeated with intermediate 2 to yield intermediate 3 where R is hexyl, phenyl, benzyl, vinyl, allyl, 1-butenyl or 1-hexenyl; and R' is isopropyl or hexyl.

EXAMPLE 12

The method of Example 8 may be repeated, with comparable results, replacing formic acid with an organic acid selected from the group consisting of citric acid, oxalic acid, chloroacetic acid, p-toluenesulfonic acid, methanesulfonic acid and trifluoroacetic acid.

EXAMPLE 13

In a polyethylene container, under nitrogen, a solution of intermediate 2 (R=$CH_3$, R'=$CH_3$), 7.2 g, in 15 ml of acetone was stirred while immersed in an ice bath at $-10°$ C. Over about 1–2 minutes, a cold ($-10°$ C.) solution of hydrofluoric acid (3 ml) in 5 ml of acetone was added from a polyethylene squirt bottle. The reaction became a brown solution shortly after the addition and was essentially complete by thin layer chromatography after 20–30 minutes at this temperature ($-10°$ C.). While stirring a total of 2 hours, the temperature of the ice bath slowly rose to 16° C. The reaction mixture was diluted with 200 ml of methylene chloride, washed with 100 ml of water and then with 50 ml of water. The combined water extracts were washed with 50 ml of fresh methylene chloride. The combined methylene chloride extracts were stirred vigorously with 200 ml of water was the pH was adjusted to 7.6 with 0.5 N sodium hydroxide solution. The layers were separated and the aqueous portion was washed with 50 ml of methylene chloride. The methylene chloride extracts were combined and dried over anhydrous sodium sulfate to which a small amount of activated charcoal was added. The mixture was filtered and concentrated to a yellow oil, 7.43 g. The crude oil was distilled under high vacuum in a Kugelrohr oven by immersing the flask containing the crude oil at 110° C. The distilled material was collected in a bulb which was cooled by wrapping it in cotton dipped in dry ice/acetone at $-72°$ C. Weight of the distilled oil intermediate 3 (R=$CH_3$, R'=$CH_3$) obtained (the product is crystalline when cooled with dry ice/acetone) was 5.34 g.

EXAMPLE 14

To a solution of 20 ml of formic acid and 1 ml of methanol at 10° C. was added dropwise 5.0 g of intermediate 2 (R=$CH_3$, R'=$CH_3$). After stirring at 10° C. for 30 additional minutes, the desired intermediate 3 (R=R'=$CH_3$) was isolated by the method of Example 8.

EXAMPLE 15

To 25 ml of acetic acid was added over 15 minutes a solution of 5.0 g of intermediate 2 (R=$CH_3$, R'=$CH_3$) in 4 ml of methanol. The reaction mixture was heated to 50° C. for 24 hours. After allowing the reaction mixture to cool to 25° C., intermediate 3 (R=$CH_3$, R'=$CH_3$), 3.19 g, was isolated by by the method of Example 8.

EXAMPLE 16

In a 3-neck roundbottom flask equipped with an addition funnel, low temperature thermometer and stirring bar was prepared a solution of 5.0 g (0.029 mol) of intermediate 2 (R=R'=$CH_3$) in 10 ml of diethyl ether and the solution was cooled to $-40°$ C. To this solution was then added dropwise 1.6 ml of concentrated sulfuric acid. The black mixture was stirred for 5 minutes at $-40°$C., poured into water and the desired intermediate 3 (R=R'=$CH_3$) isolated by the method of Example 8.

Substantially the same results may be obtained replacing sulfuric acid with hydrochloric acid or phosphoric acid.

EXAMPLE 17

To a dry flask was added 1.05 grams (0.0074 mol) of intermediate 3 (R=$CH_3$, R'=$CH_3$) dissolved in 20 ml of isopropyl alcohol and the flask cooled to 0° C. Then 0.5 g (0.0059 mol) of sodium bicarbonate and 2.0 ml (0.023 mol) of 30% hydrogen peroxide were added and the reaction mixture allowed to stir at room temperature for about 2 hours. The reaction mixture was poured into 100 ml of water, extracted with chloroform and the chloroform extract concentrated to yield 0.90 g (77%) of intermediate 4 (R=R'=$CH_3$) as a yellow oil which could be distilled at 70°–90° C./3 mm. An analytical sample was purified by gas chromatography.

| | Analysis: | |
|---|---|---|
| | C | H |
| Calc'd. for $C_7H_{10}O_4$: | 53.16 | 6.37 |
| Found: | 52.90 | 6.27 |

EXAMPLE 18

The method of Example 17 was repeated with intermediate 3 (R=H, R'=$CH_3$) to yield intermediate 4 (R=H, R'=$CH_3$).

| | Analysis: | |
|---|---|---|
| | C | H |
| Calc'd. for $C_6H_8O_4$: | 50.00 | 5.59 |
| Found: | 50.09 | 5.81 |

EXAMPLE 19

The method of Example 17 was repeated with intermediate 3 (R=$CH_2CH_3$, R'=$CH_3$) to yield intermediate 4 (R=$CH_2CH_3$, R'=$CH_3$).

| | Analysis: | |
|---|---|---|
| | C | H |
| Calc'd. for $C_8H_{12}O_4$: | 55.81 | 7.02 |
| Found: | 55.95 | 7.04 |

EXAMPLE 20

The method of Example 17 may be repeated with intermediate 3 to yield intermediate 4 where R is hexyl, phenyl, benzyl, vinyl, allyl, 1-butenyl and 1-hexenyl; and R' is isopropyl and hexyl.

EXAMPLE 21

To a 75 ml flask was added 2.84 g. (0.02 mol) of intermediate 3 (R=$CH_3$, R'=$CH_3$), 10 ml of water and 10 ml of isopropanol. The solution was cooled to 0°–5° C., and the pH adjusted to 7.0–9.0 with 1 N NaOH. Then 2.1 ml of 30% hydrogen peroxide was added dropwise, with NaOH also added as necessary to maintain constant pH. Cooling was necessary to keep the pot temperature below 10° C. After the addition of peroxide, the reaction was stirred at 8°–10° C. for about one hour, poured in water and the solution extracted with chloroform. Solvent removal yielded 2.99 g. (94.5%) of the intermediate 4 (R=$CH_3$, R'=$CH_3$) as a clear oil. Reaction temperatures above 15° C. and a pH above 9.5 or below 6.5 result in lower yields of intermediate 4.

Substantially the same results are obtained replacing isopropanol with water.

EXAMPLE 22

To a flask with a condenser was added 3.7 g. (0.023 mol) of intermediate 4 (R=CH₃, R'=CH₃) and 50 ml of 2 M H₂SO₄. After heating this two phase solution for 1.5 hours at reflux (95°–100° C.), the reaction cooled, adjusted to pH 2.2 with 6 N NaOH, extracted 3 times with 100 ml volumes of chloroform and the combined solvent extracted concentrated to yield product 5 (R=CH₃).

EXAMPLE 23

The method of Example 22 may be repeated with intermediate 4 where R is hydrogen, ethyl, hexyl, phenyl, benzyl, allyl, vinyl, 1-butenyl and 1-hexenyl; and R' is methyl, ethyl, isopropyl and hexyl to yield product 5 where R is hydrogen, ethyl, hexyl, phenyl, benzyl, allyl, vinyl, 1-butenyl and 1-hexenyl.

EXAMPLE 24

To a 250 cc Wheaton pressure bottle was added 3.16 g. (0.02 mol) of intermediate 4 (R=CH₃, R'=CH₃) and 50 cc of 2 M H₂SO₄. The vessel was sealed and heated to 140°–160° for 1–2 hours. After cooling, the reaction was processed as in Example 22 to yield maltol (R=CH₃).

EXAMPLE 25

The method of Examples 22 and 23 may be repeated, with comparable results, replacing sulfuric acid with hydrochloric acid, Dowex 50W or Amberlite GC-120.

EXAMPLE 26

To a small flask was added 1.58 g. (0.01 mol) of intermediate 4 (R=CH₃, R'=CH₃) and 25 ml of benzene followed by 3.7 ml of boron trifluoride etherate. After stirring for 24 hours at 25° C., the solvent was removed, the residue extracted with chloroform, and the chloroform removed to yield maltol (R=CH₃).

Substantially the same results are obtained when boron trifluoride etherate is replaced with p-toluenesulfonic acid, formic acid, zinc chloride or tin tetrachloride.

What is claimed is:

1. A process for preparing a compound of the formula

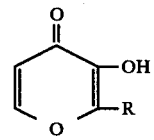

wherein R is hydrogen, alkyl or 1 to 6 carbon atoms, alkenyl of 2 to 6 carbon atoms, phenyl or benzyl which comprises contacting a compound

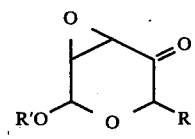

wherein R is as defined above and R' is alkyl of 1 to 6 carbon atoms, at 25° to 160° C. with an acid substance selected from the group consisting of sulfuric acid, hydrochloric acid, boron trifluoride etherate, p-toluenesulfonic acid, formic acid, zinc chloride and tin tetrachloride.

2. A process of claim 1 wherein both R and R' are methyl.

3. A process of claim 1 wherein R is ethyl and R' is methyl.

4. A process of any one of claim 1 or claim 2 or claim 3 wherein the acid is hydrochloric acid.

* * * * *